(12) United States Patent
Fregoso et al.

(10) Patent No.: US 9,931,187 B2
(45) Date of Patent: Apr. 3, 2018

(54) PHOTON INDUCED ACOUSTIC STREAMING DEVICE AND METHOD

(71) Applicant: AMERICAN EAGLE INSTRUMENTS, INC., Missoula, MT (US)

(72) Inventors: Gilbert Fregoso, Missoula, MT (US); Brad B. Heckerman, Missoula, MT (US)

(73) Assignee: Brad Heckerman, Lakeside, MT (US)

( * ) Notice: Subject to any disclaimer, the term of this patent is extended or adjusted under 35 U.S.C. 154(b) by 498 days.

(21) Appl. No.: 14/385,832

(22) PCT Filed: Nov. 29, 2012

(86) PCT No.: PCT/US2012/066925
§ 371 (c)(1),
(2) Date: Sep. 17, 2014

(87) PCT Pub. No.: WO2013/151585
PCT Pub. Date: Oct. 10, 2013

(65) Prior Publication Data
US 2015/0056567 A1 Feb. 26, 2015

Related U.S. Application Data

(60) Provisional application No. 61/620,718, filed on Apr. 5, 2012.

(51) Int. Cl.
*A61C 19/06* (2006.01)
*A61C 17/02* (2006.01)
*A61C 5/40* (2017.01)

(52) U.S. Cl.
CPC ............... *A61C 19/06* (2013.01); *A61C 5/40* (2017.02); *A61C 17/02* (2013.01)

(58) Field of Classification Search
CPC ........... A61C 17/02; A61C 13/15; A61C 5/40; A61C 19/06; A61C 5/04; A61C 19/00;
(Continued)

(56) References Cited

U.S. PATENT DOCUMENTS 5,634,711 A 6/1997 Kennedy et al.
6,159,005 A 12/2000 Herold et al.
(Continued)

FOREIGN PATENT DOCUMENTS

JP 2004275276 A 10/2004
WO 2002069839 A1 12/2002
(Continued)

OTHER PUBLICATIONS

Supplementary European Search Report issued for European Patent Application No. EP 12873729 dated Nov. 9, 2015.
(Continued)

*Primary Examiner* — Nicholas Lucchesi
(74) *Attorney, Agent, or Firm* — Heslin Rothenberg Farley & Mesiti P.C.

(57) ABSTRACT

A device and method of using a device for photon-induced endodontic and periodontic applications includes a power source, a trigger coupled to the power source and circuit elements initiated by the trigger. The circuit elements include a timing circuit and a driver. A light source is coupled to the circuitry elements wherein and driver controls the period, cycle, and pulse generation of the light source to create photon induced acoustic waves. The optical assembly includes a fiber optic cable and an output tip and is coupled to the light source. This optical assembly refracts light from the light source and photon induced acoustic waves exit the output tip in a pre-determined pattern.

20 Claims, 8 Drawing Sheets

(58) Field of Classification Search
CPC .. A61C 1/00; A61C 1/16; H05B 33/08; A61N 5/06; B25B 33/00
See application file for complete search history.

(56) References Cited

U.S. PATENT DOCUMENTS

| | | | |
|---|---|---|---|
| 6,880,954 B2 | 4/2005 | 011Ett et al. | |
| 7,029,277 B2 | 4/2006 | Gofman et al. | |
| 7,101,072 B2 | 9/2006 | Takada et al. | |
| 7,210,930 B2 | 5/2007 | Kovac et al. | |
| 7,226,470 B2 | 6/2007 | Kemeny et al. | |
| 7,535,184 B1 * | 5/2009 | Fregoso | A61C 19/004 315/224 |
| 7,748,979 B2 | 7/2010 | Nahlieli | |
| 7,789,661 B2 | 9/2010 | Ostler et al. | |
| 7,857,619 B2 | 12/2010 | Liu | |
| 2003/0215766 A1 | 11/2003 | Fischer et al. | |
| 2003/0235800 A1 | 12/2003 | Qadar | |
| 2006/0085052 A1 | 4/2006 | Feuerstein et al. | |
| 2006/0252005 A1 | 11/2006 | Feinbloom et al. | |
| 2007/0072153 A1 | 3/2007 | Gross et al. | |
| 2009/0130622 A1 | 5/2009 | Bollinger et al. | |
| 2010/0167226 A1 | 7/2010 | Altshuler et al. | |
| 2010/0330523 A1 | 12/2010 | Kert | |
| 2010/0330539 A1 * | 12/2010 | Glover | A61B 18/20 433/224 |
| 2011/0111365 A1 * | 5/2011 | Gharib | A61C 5/40 433/81 |
| 2012/0123399 A1 * | 5/2012 | Belikov | A61B 18/201 606/16 |
| 2012/0237893 A1 * | 9/2012 | Bergheim | A61C 5/02 433/81 |
| 2013/0040267 A1 * | 2/2013 | Bergheim | A61C 3/03 433/216 |
| 2014/0099597 A1 * | 4/2014 | Bergheim | A61C 17/02 433/80 |
| 2014/0220505 A1 * | 8/2014 | Khakpour | A61C 17/02 433/81 |
| 2015/0010882 A1 * | 1/2015 | Bergheim | A61C 17/02 433/80 |

FOREIGN PATENT DOCUMENTS

| | | |
|---|---|---|
| WO | 2010051579 A1 | 5/2010 |
| WO | 2010132496 A1 | 11/2010 |

OTHER PUBLICATIONS

International Search Report for PCT/US2012/066925 dated Mar. 22, 2013.
Cobb, "Lasers in Periodontics: A Review of the Literature", AAP-Commissioned Review, School of Dentistry, University of Missouri, Kansas City, MO, vol. 77, No. 4. Apr. 2006, pp. 545-564.
Goldstep et al., Diode Lasers for Periodontal Treatment—The Story Continues. Dental Asia, Jul./Aug. 2011, pp. 20-23.
Liz Lundry, "Lasers in Hygiene—Shine the Healing Light" Mar. 1, 2010, 10-pages.
Scott D. Benjamin, DDS, "Soft Tissue Lasers: It's the Wavelength, Power, Ergonomics, and Control That Matter!" 11-pages.
Fay Goldstep, "Diode Lasers for Periodontal Treatment: The Story So Far", Orah Health Journal, Dec. 2009, pp. 44-46.
Chapter 5: Characterisation of the NIR Water Absorption Spectrum.

* cited by examiner

PHOTON INDUCED ACOUSTIC STREAMING DEVICE AND METHOD

CROSS-REFERENCE TO RELATED APPLICATIONS

This application is a National Stage application based on International Application PCT/US2012/066925 filed on Nov. 29, 2012, published as WO 2013/151585 A1 on Oct. 10, 2013. This application also claims the benefit of U.S. Provisional Application No. 61/620,718, filed Apr. 5, 2012, which are incorporated herein by reference.

FIELD OF INVENTION

The present invention relates to an apparatus and method of a utilizing a light source to pulse fluid for irrigation and cleansing for periodontic and endodontic procedures.

BACKGROUND OF INVENTION

In both periodontics and endodontics, effective irrigation of tissue and surrounding structures makes effective cleaning and disinfection possible. Irrigation is accomplished by agitating fluid. In periodontic procedures, such as gum surgery and in endodontic procedures, such as root canals, this agitation and irrigation eradicates bacteria and lessens the chance of infection. Agitating fluid causes disturbances, i.e., vibrations, that force out debris and other foreign particles that could irritate the area and lead to infection. By creating disturbances in saliva and fluids already in the cavities and/or cleansing chemicals that are added, such as hydrogen peroxide, the foreign particles and debris can be forced out of sensitive areas. For example, effective endodontic treatment requires the combination of physical and chemical agents to eradicate soft-tissue debris, smear layer, and microorganisms. In root canals, antimicrobial irrigants are commonly used.

Different agitation techniques have been proposed to improve the efficacy of irrigation solutions, including agitation with hand files, gutta-percha cones, plastic instruments, and sonic and ultrasonic devices. Photon-initiated photoacoustic streaming (PIPS®) refers to the use of a laser as a pulsing light source to create the agitation to irrigate areas in both endodontic and periodontic procedures. Acoustic streaming is a steady current in a fluid driven by the absorption of high amplitude acoustic oscillations. Photo acoustic streaming utilizes photons to induce oscillations.

PIPS® utilizes an erbium YAG laser, Er:YAG laser, (erbium-doped yttrium aluminum garnet laser) to activate irrigation solutions by the transfer of pulsed energy to agitate fluid and increase the efficacy or irrigation. This method has produced mixed results. Although some positive results have emerged as far as the elimination of bacteria, the use of Er:YAG lasers present a number of challenges including both cost and efficacy. For example, in an Er:YAG laser, the unidirectional emission of the laser beam makes it difficult to access the entire root canal wall with the Er:YAG laser. Additionally, a given Er:YAG laser can only project one wavelength and different dental procedures may benefit from using different wavelengths, and more than one wavelength at a given time. Due to the challenges presented by Er:YAG lasers, the capacity of PIPS® to disinfect root canals, and other sites that would benefit from irrigation, has not been established. Also, using an Er:YAG laser for this application may be cost-prohibitive for many dental practitioners.

Another challenge of using a laser, or any light source, in an irrigation solution is the potential for creating hot spots in the solution, and therefore in the mouth of a patient, which can lead to tooth and gum damage. When the light leaving the irrigation device and comes into contact with liquid in the mouth, such as a solvent, or water, the heat generated can converge in solution, creating a hot spot. This hot spot can cause pain as well as damage dental structures.

Unlike in endodontic applications, Laser Assisted Periodontal Therapy (LAPT) has been used effectively to battle periodontal disease. However, the wavelengths, pulse rates, and power settings utilized in periodontal treatments are presently incompatible with those attempted in endodontic applications.

Periodontal disease is a chronic inflammatory disease caused by bacterial infection. The inflammation is the body's response to destroy, dilute or wall off the injurious agent. Unfortunately, this response destroys the tissue. The periodontal pocket, in periodontal disease, contains several substances that contribute to the continuation of the unhealthy condition: calculus and plaque on the tooth surface, pathogenic bacteria, and/or an ulcerated, epithelial lining with granulation tissue and bacterial by-products.

Treatments for periodontal disease include scaling and root planing (SRP), which eliminates calculus, plaque and other debris on the tooth to create a totally clean surface, decontamination, which eliminated all pathogenic bacteria dispersed through the pocket, curettage, which eliminates granulation tissue, bacterial products, and ulcerated areas to create a clean, even epithelial lining without tissue tags, and biostimulation.

Laser sulcular debridement is used as an adjunct therapy to conventional root planing and scaling. The purpose is to remove the diseased epithelium of the periodontal pocket, leaving the healthy tissue intact. The diode laser is effective in treating diseased soft tissue. The diode laser energy is well absorbed by melanin, hemoglobin and other chromophores that are present in periodontal disease. By adding use of photo acoustic streaming with a laser diode as a light source, to SRP, the results in periodontal treatments have been significantly improved.

LAPT presents at least the following advantages over traditional surgical SRP: longer lasting results, decreased gingival bleeding, decreased inflammation, improved pocket depth, decreased tooth mobility and clinical attachment loss. LAPT can also reduce or eliminate the need for antibiotic post SRP or surgical treatments. In LAPT, there are no adverse effects to tissue, roots of the tooth, or cementum due to thermal side effects or the light beam itself.

This therapy utilizes the light energy emitted by the laser elicits beneficial cellular and biological responses. This therapy is effective on a cellular and a bactericidal level. On a cellular level, metabolism is increased, stimulating the production of ATP (adenosine triphosphate), increasing the energy available to normalize cell function and promote tissue healing. On the bactericidal level, the laser energy reduce and/or eliminates the bacteria of the periodontal pocket, including the sulcular wall, as much as possible and to form a stable clot.

A need exists for a system and method for photon-induced acoustic streaming for both endodontic and periodontic dental applications that is effective, affordable, and safe.

SUMMARY OF INVENTION

An object of the present invention is to utilize affordable infrared (IR) light sources to produce photon-induced acoustic streaming capable or irrigating dental canals for endodontic applications, and for treating diseased tissue and eliminating bacteria in periodontic applications.

An object of the present invention is to utilize a range of light waves (600 nm-1,500 nm) for treating diseased tissue and eliminating bacteria in periodontic applications.

Another object of the present invention is to simultaneously use more than one wavelength in photon-induced acoustic streaming capable of irrigating dental canals for endodontic applications and/or treating diseased tissue and eliminating bacteria in periodontic applications.

Another object of the present invention is to utilize photon-induced acoustic streaming in periodontic applications. Another object of the invention is to provide LAPT both with and without the use of a photo acoustic streaming.

Another object of the present invention is to provide photon-induced acoustic streaming capable or irrigating dental canals for endodontic applications and treating diseased tissue and eliminating bacteria in periodontic applications in a manner that is safe and preserves the dental health of a patient.

An embodiment of the present invention is a photon-induced acoustic streaming device for endodontic and periodontic applications which includes a power source, a trigger coupled to the power source and circuit elements initiated by the trigger. The circuit elements include a timing circuit and a driver. A light source is coupled to the circuitry elements wherein and driver controls the period, cycle, and pulse generation of the light source to create photon induced acoustic waves. The optical assembly includes a fiber optic cable and an output tip and is coupled to the light source. This optical assembly refracts light from the light source and photon induced acoustic waves exit the output tip in a pre-determined pattern.

An embodiment of the present invention is a method for utilizing a photon-induced acoustic streaming device for periodontic and endodontic procedures. The method includes: engaging a trigger on a handheld assembly of the device described above to trigger the light source to emit light at a first predetermined wavelength; positioning a lower portion of the previously described output tip in an irrigation fluid to emit photon induced acoustic waves from the lower portion of said output tip into the irrigation fluid to irrigate dental canals and structures coming into contact with the irrigation fluid; adjusting the wavelength to trigger said light source to emit light at a second predetermined wavelength; and positioning the lower portion of the output tip proximate to diseased tissue to emit photon induced acoustic waves the said lower portion of the output tip into the diseased tissue to eliminate bacteria in the diseased tissue.

A further embodiment of the present invention is a method for utilizing a photon-induced acoustic streaming device for periodontic and endodontic procedures. The method includes: engaging a trigger on a handheld assembly of the device described above to trigger the light source to emit light at a first predetermined wavelength; positioning a lower portion of the previously described output tip in an irrigation fluid to emit photon induced acoustic waves from the lower portion of said output tip into the irrigation fluid to irrigate dental canals and structures coming into contact with the irrigation fluid; adjusting at least one of the repetitive rate, duty cycle, and pulse duration of said device; and positioning the lower portion of the output tip proximate to diseased tissue to emit photon induced acoustic waves from the lower portion of the output tip into the diseased tissue to eliminate bacteria in the diseased tissue.

Acoustic streaming is a steady current in a fluid driven by the absorption of high amplitude acoustic oscillations. The apparatus and method of the present invention focus a light source to a point to bring the light to the intensity used to perform the infrared (IR) vibrational absorption useful in various dentistry-related applications. In an embodiment of the present invention, at least one fiber optic cable and an output tip are utilized to apply the vibrations. Light sources used in various embodiments of the present invention include, but are not limited to, incandescent light bulbs, high intensity discharge lamps (HIDs), light-emitting diodes (LEDs), and laser diodes.

An embodiment of the present invention utilizes an infrared (IR) incandescent lamp as a photo-acoustic source. This embodiment comprises an AC or a DC input voltage powering at least one IR incandescent lamp, which is modulated by a motorized period cycle and pulse generator. Light passing through the motorized period cycle and pulse generator is gathered and focused by at least one optic lens, reflector, mirror, or prism. The focused light travels through a fiber optics cable and to a hand piece that holds an output tip, which refracts the light at a desired angle or angles.

An embodiment of the present invention utilizes one or more HIDs as a photo-acoustic source. As power converters and sources, this embodiment comprises an AC or DC, a DC voltage power supply, a power factor controller (PFC) circuit, to control the HID lamp's current and voltage, a bridge inverter, and a high voltage igniter. A motorized period cycle and pulse generator pulses the light, while at least one optic lens, reflector, mirror, and/or prism focuses the light output. The focused light travels through a fiber optics cable, which feeds this focused light to the hand piece, that holds an output tip. The output refracts the light at a desired angle or angles of refraction.

An embodiment of the present invention utilizes a multi-wavelength LED array (die) as a source of photons for acoustic streaming. This embodiment is powered by an AC or DC input and a DC voltage power supply. An LED driver controls the period, cycle, and pulse generation. The light source is focused by an optical device, such as a lens, reflector, mirror and/or prism and travels through a fiber optics assembly, to a fiber optic cable attached to a hand piece which holds a removable tip. The tip refracts the light into the liquid in a pre-determined desired pattern.

An embodiment of the present invention utilizes one or more laser diodes as a photo-acoustic source. This embodiment is powered by an AC or DC input and comprises a hand piece housing attached to an optical housing assembly, which includes a tip. In the hand piece housing, a start/stop mechanism, including but not limited to, a switch, initiates a timing circuit and a laser power driver for the laser diode, controlling the period, cycle, and pulse generation. The light source is focused by an optical device, such as a lens, reflector, mirror and/or prism and travels through a fiber optics assembly, to a fiber optic cable attached to a hand piece which holds a removable tip. The tip refracts the light into the liquid in a pre-determined desired pattern.

Embodiments of the present invention feature tips that can be disposed of and/or sterilized. An embodiment of the tip includes two optic housings. The first housing establishes the direction of the light and the second insulates the light from the liquid so that the angle can be maintained and the light emitted from the tip will not create a hot spot in the mouth of a patient.

In an embodiment of the present invention, the tip can be substituted with a different tip depending upon the use on the instrument, whether periodontic or endodontic and the specific application.

In one embodiment of the present invention, three tips are utilized for a variety of applications. In this embodiment, the first tip is the Photo Induced Streaming Tip, which is designed to send a photo acoustical shock wave through irrigation materials, including but not limited to, a solution of 17% Ethylenediaminetetraacetic acid (EDTA), or 5.25% sodium hypochlorite. The second tip the Perio High Energy Tip, which is designed to decontaminate and eliminate pathogenic bacteria dispersed through the pocket and on the tooth structure. The third tip is the Perio Biostimulation Tip, which is designed to biostimulate cell function and repair to promote increased lymphatic flow, production of endorphins, increased microcirculation, increased collagen formation and the stimulation of fibroblasts.

In an embodiment of the present invention, a wavelength of 950-980 nm is utilized in both endodontic and periodontic applications.

Although the present invention has been described in relation to certain incandescent, HID, LED, and laser diode light sources, many other variations and modifications will become apparent to those skilled in the art, including coupling the tip with additional light sources.

DETAILED DESCRIPTION OF THE INVENTION

The apparatus and method of the present invention focus a light source to a point to bring the light to the intensity used to perform the infrared (IR) vibrational absorption useful in various dentistry-related applications. In an embodiment of the present invention, at least one fiber optic cable and an output tip are utilized to apply the vibrations.

The system and method of the present invention utilizes lower-powered affordable light sources in combination with custom tips to pulse fluid for endodontic and/or, periodontic procedures. Specifically, these light sources, through photo acoustic streaming, provide a steady current in a fluid driven by the absorption of these high amplitude acoustic oscillations.

These light sources, which are of the infrared vibrational absorption spectrum of liquid water, are coupled with removable and/or sterilized tips, which render the procedure more hygienic. Light sources used in various embodiments of the present invention include, but are not limited to, incandescent light bulbs, high intensity discharge lamps (HIDs), light-emitting diodes (LEDs), and laser diodes.

Various embodiments of the present invention pulse a variety of liquids effective for irrigation, dissolving tissue, and cleaning the smear layer. Liquids used in conjunction with these embodiments include, but are not limited to, water, and various sodium solutions, including 5.25% sodium hypochlorite (NaOCL), 2% cholorhexidine gluconate, 17% ethylene diamine tetra acetic acid (EDTA), or 10% citric acid.

Figure 1:
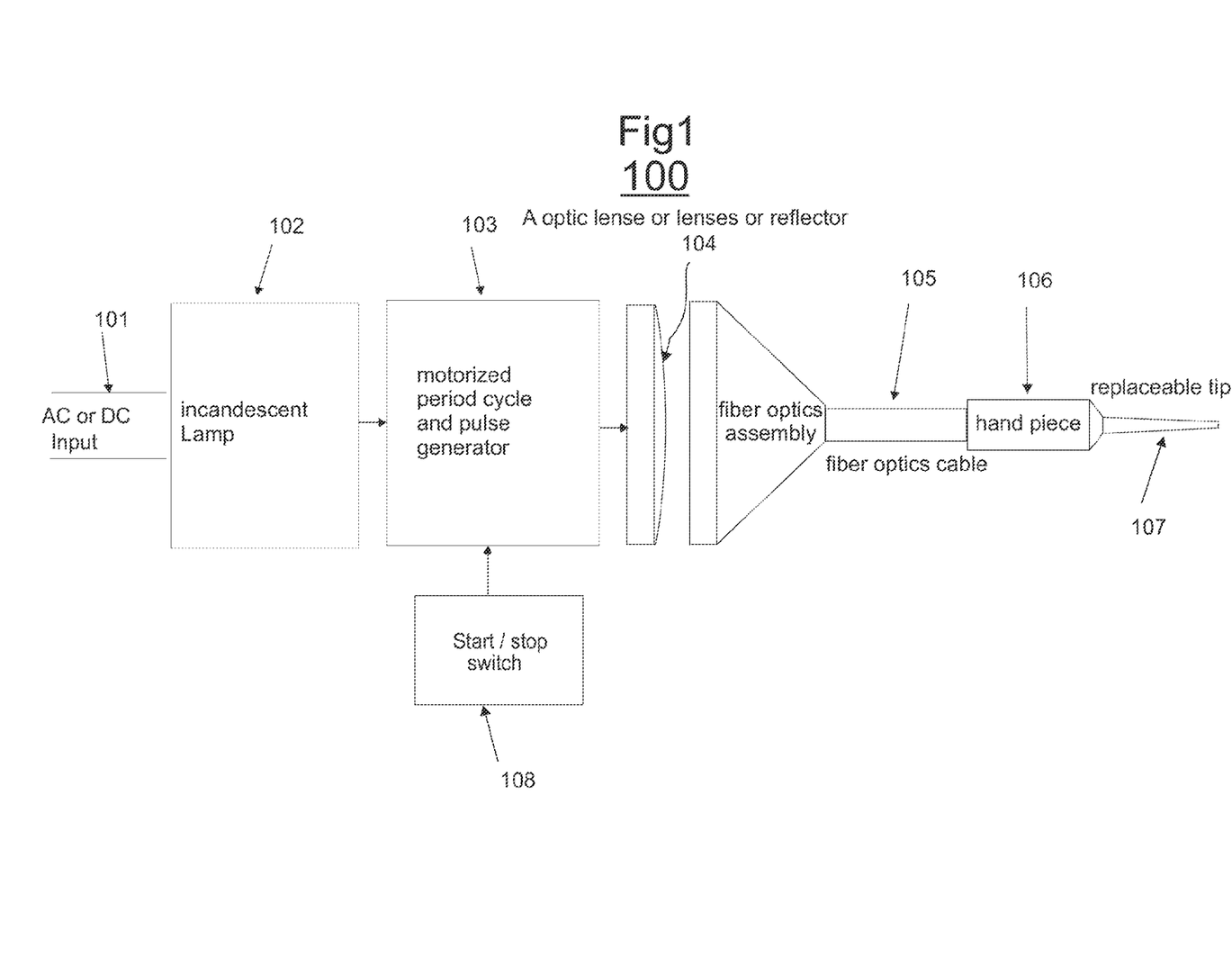
FIG. 1 depicts an embodiment of the present invention.

FIG. 1 is an embodiment of the present invention, a device 100 utilizing an infrared (IR) incandescent lamp as a photo-acoustic source. The power source in this embodiment 101 includes but is not limited to an AC or a DC input voltage. The power source powers the IR incandescent lamp 102. Although the embodiment of FIG. 1 utilizes a single IR incandescent lamp 102, further embodiments of the present invention utilize additional light sources dependent upon the applications and desired output from the light source.

The light from the IR incandescent lamp 102 is modulated by a motorized period cycle and pulse generator 103. A motorized period cycle and pulse generator 103 is a low cost and simplistic modulator (it is a disk with holes and a motor that turns the disk), and its simplicity assists in realizing the cost advantages of this embodiment.

Light passing through the motorized period cycle and pulse generator 103 is gathered and focused by at least one optic lens 104. One of skill in the art will recognize that further embodiments of the present invention can utilize different structures with equivalent functionality to this optic lens 104 to gather and focus light, including but not limited to one or more reflectors, mirrors and/or more prisms, and/or a combination of these items.

In the embodiment of FIG. 1, coupled to the motorized period cycle and pulse generator 103 is a start/stop switch 108. The start/stop switch 108 is located on the underside of the device 100 for ease of operation. The position of the access point to the start/stop switch 108 can be customized for individual operators depending on qualities of the operators. For example, one position may be less convenient for an operator who is left-handed, while it is most convenient for an operator who is right-handed.

In this embodiment, by coupling the start/stop switch 108 to the motorized period cycle and pulse generator 103, the acoustic streaming can be halted without turning the light source off. An incandescent light source has a higher failure rate if it is turned on and off rapidly; the light source is preserved if there is a lag, for example, 45 seconds, before making this type of adjustment. In this embodiment of the invention, to preserve the light source, the source is pulsed using a motorized period cycle and pulse generator 103, instead of switching the source itself on and off. Thus, by turning the motorized period cycle and pulse generator 103 off and leaving the light source, e.g., the incandescent lamp 102, on, the longevity of the light source, incandescent lamp 103, for the device 100 is preserved.

Returning to FIG. 1, after the light is gathered and focused by the optic lens 104, the light travels through a fiber optics cable 105, which feeds this focused light to the hand piece 106, that holds the output tip 107. The output tip 107 is the exit point for the light. At the exit point, the output tip 107 refracts the light at a desired angle (or multiple angles) of refraction. The output tip 107 is discussed in greater detail in reference to FIG. 5. The material comprising the tip includes, but is not limited to, plastic and/or glass, and/or a crystal material (sapphire, quartz, etc.).

Figure 2:
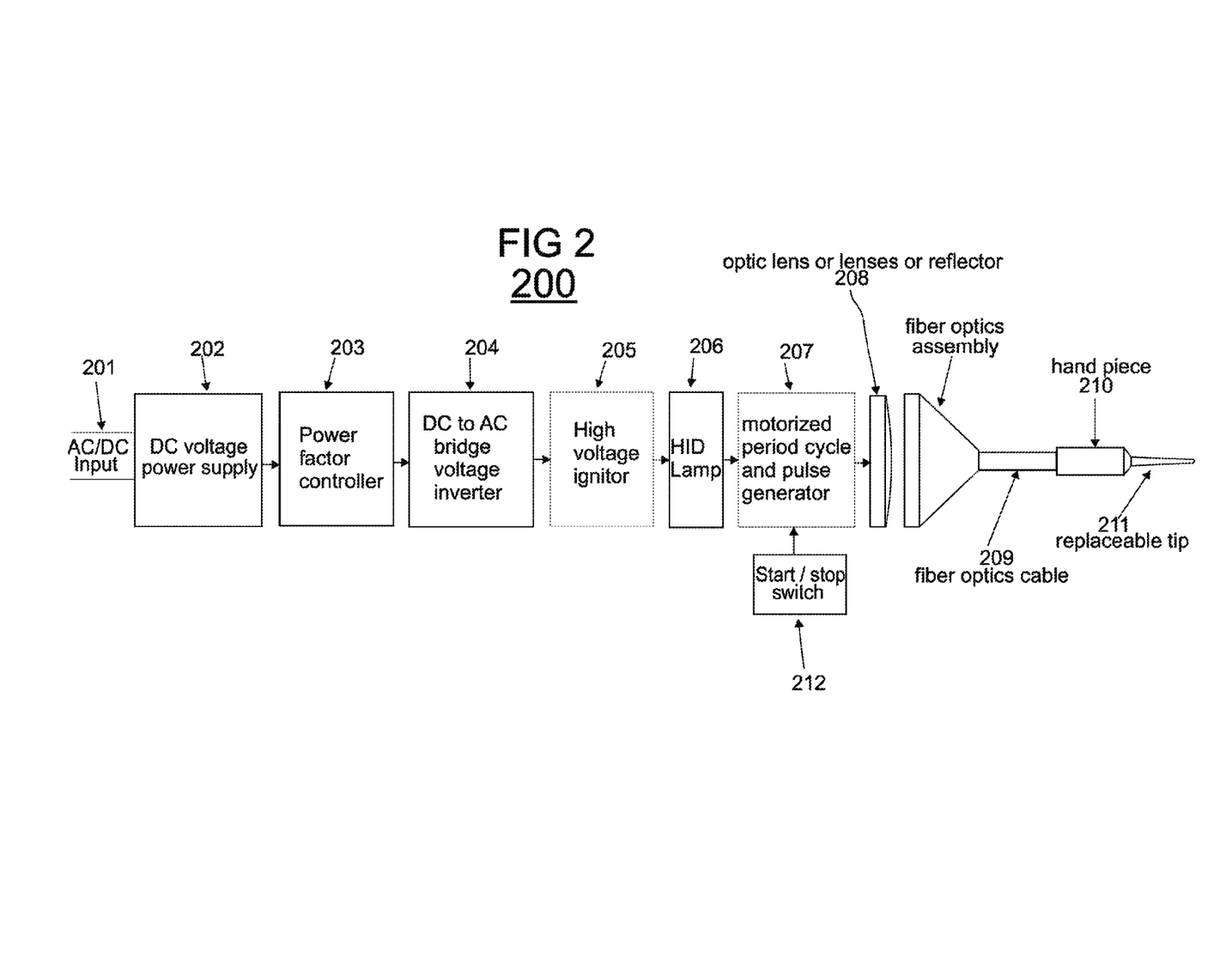
FIG. 2 depicts an embodiment of the present invention.

FIG. 2 is an embodiment of the present invention, a device 200 utilizing one or more HIDs as a photo-acoustic source. FIG. 2 depicts a single HID lamp, however, additional embodiments of the present invention may utilize more than one HID lamp.

This device 200 is compatible with both an AC or DC input 201, which is coupled to a DC voltage power supply 202; the power supply 202 is the power supply for all the integrated circuits (ICs) and the motorized period cycle and pulse generator 207.

In this embodiment, the power factor controller 203 (PFC) circuit controls the HID lamp's current and voltage. The PFC 203 is included with the use of an HID lamp 206 because HID lamps vary. One embodiment of the present invention utilizes a custom HID lamps with a 1950 nm light spectrum.

The HID lamp 206 is powered by an AC square wave. Thus, before the power reaches the HID lamp 206, it is converted from DC to the AC square wave by a bridge inverter 204. The next element of the device 200 is a high voltage igniter 205, which breaks down the gases in the HID lamp 206.

This HID-powered embodiment also utilizes a motorized period cycle and pulse generator 207 to modulate the light from the HID lamp 206. Similar to the device 100 in FIG. 1, the start/stop switch 212 in this device is coupled to the motorized period cycle and pulse generator 207 so that modulation can be controlled without immediately turning off the light source, the HID lamp 206, itself.

Referring to FIG. 2, light passing through the motorized period cycle and pulse generator 207 is gathered and focused by at least one optic lens 208. One of skill in the art will recognize that further embodiments of the present invention can utilize different structures with equivalent functionality to this optic lens 208 to gather and focus light, including but not limited to one or more reflectors, mirrors and/or more prisms, and/or a combination of these items.

Like in the embodiment of FIG. 1, in the embodiment of FIG. 2, after the light is gathered and focused by the optic lens 208, the light travels through a fiber optics cable 209, which feeds this focused light to the hand piece 210, that holds the output tip 211. The output tip 211 refracts the light at a desired angle (or angles) of refraction so that light can induce oscillations in the liquid, including but not limited to, water. The material comprising the tip includes but is not limited to plastic and/or glass.

Figure 3:
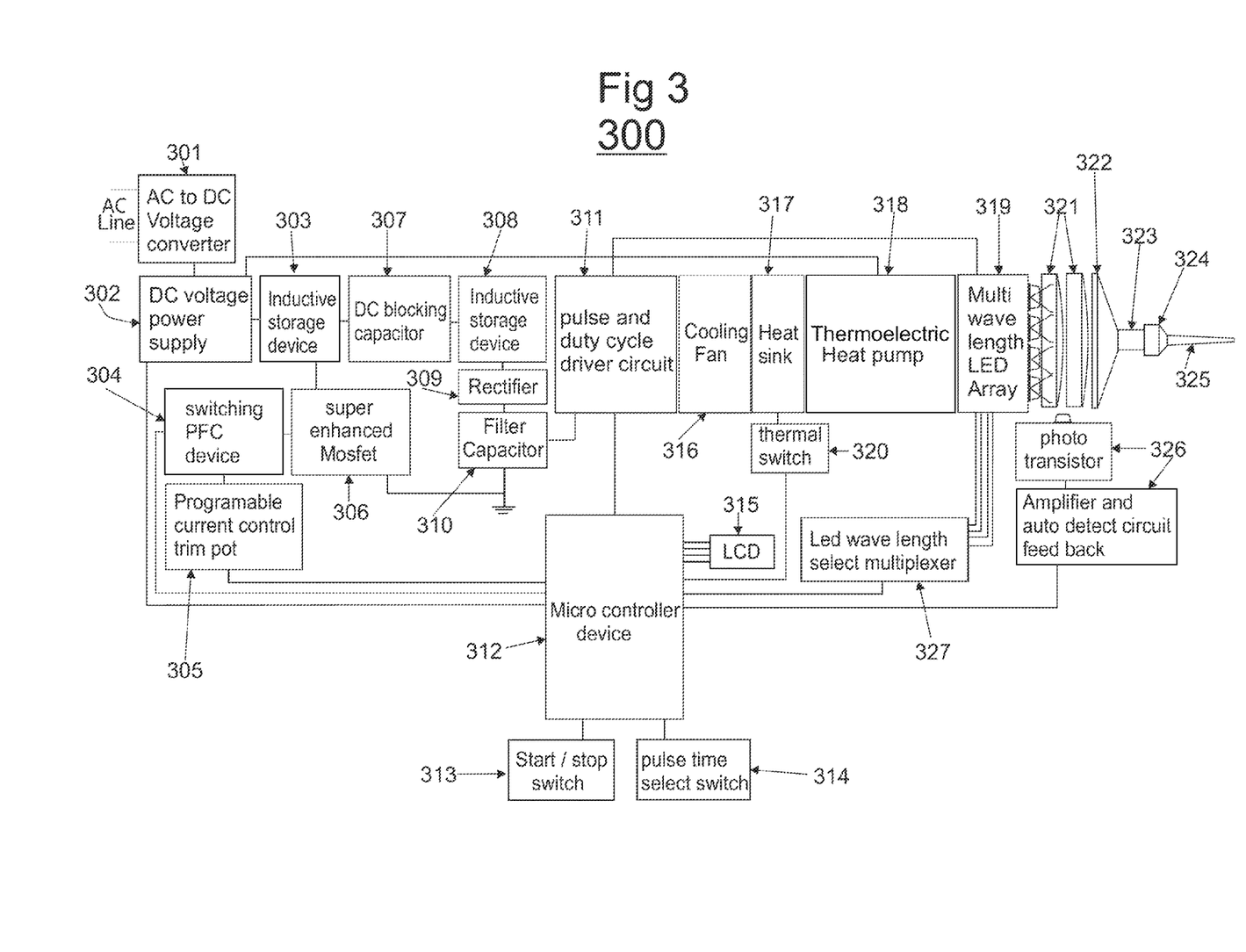
FIG. 3 depicts an embodiment of the present invention.
Figure 4:
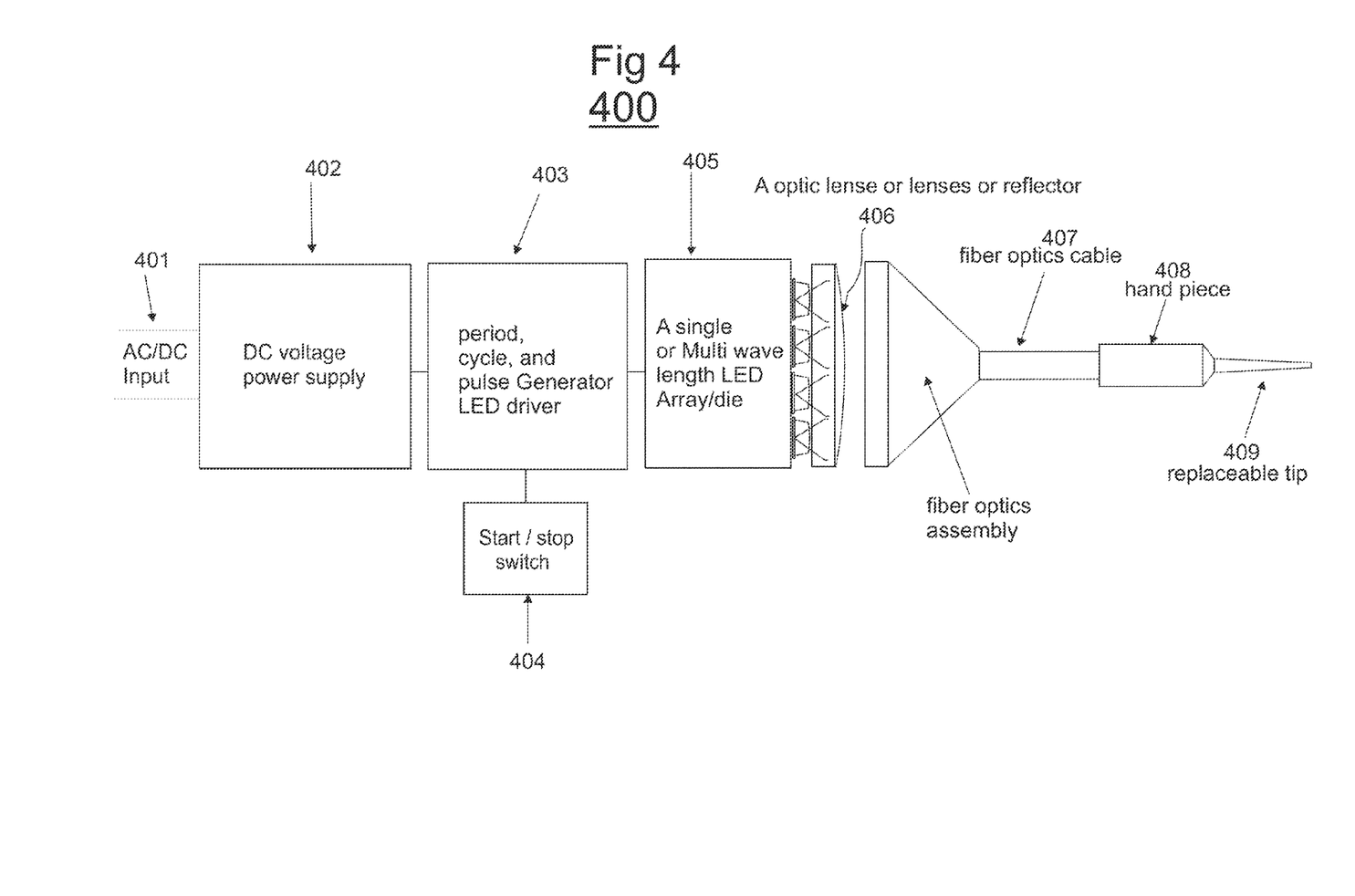
FIG. 4 depicts an embodiment of the present invention.

FIGS. 3-4 are two different embodiments of the present invention that utilize LEDs as light sources in photon induced acoustic streaming. These two embodiments are described by way of example. One of skill in the art will recognize that the embodiments of these figures are not meant to encompass all embodiments utilizing LED light sources in the light spectrum of vibrational absorption spectrum of liquid water, which embody the apparatus and practice the system and method claimed, and that additional variants thereof employ the concepts of these enumerated embodiments.

Referring to FIG. 3, the device 300 utilizes a multi-wavelength LED array (die) 319 as a source of photons for acoustic streaming. Because the multi-wavelength LED array 319, is capable of producing more than one wavelength, the device 300 is flexible across different applications. The spectrum of the multi-wavelength LED array 319 can be focused on one, two, or more wavelengths to produce the desired photo acoustic shock effect. The device 300 also includes a power correction circuit, and cooling components to manage the current, voltage, and heat.

LED light source configurations operational in various embodiments of the present invention include, but are not limited to, one or more LEDs mounted in an optical housing, one or more LEDs mounted on a PCB with an optical housing, and/or one or more LED dies mounted on a PCB with an optical housing.

The device 300 gains power input from an AC line and uses an AC to DC converter 302. In embodiments of the present invention, the AC line input is 86 VAC to 240 VAC 50/60 Hz with a front end line filter. The device 300 also utilizes a low voltage power supply 302 that supplies power to all the IC supplies. In embodiments of the present invention, the power supplies are 5 VDC and 15 VDC. The device 300 also utilizes an inductive storage device 303, which is an inductor/transformer and is designed to switch at resonance.

A switching PFC device, including but not limited to a Power Factor Correction ANA PFC, is coupled to a Digital Potentiometer ICs 305. The Digital Potentiometer ICs 305, which takes instruction from the micro controller device 312 to set the output power.

Referring to FIG. 3, also included in the power correction circuit of the device 300 is a switching metal-oxide-semiconductor field-effect transistor (Mosfet) Transistor 306, i.e., a super enhanced Mosfet, utilized to switch the inductive load, and a DC blocking capacitor 307. A second inductive storage device 308 is also part of the Power Factor Correction circuit. This inductor/transformer is used to lower the voltage and it resonates with the inductive storage device 303. After this second inductive device 308 corrects the power, a rectifier 309 is utilized to convert the AC to DC. A filter capacitor 310 filters the DC. A pulse and duty cycle driver IC 311 is utilized to drive the Mosfet 6. This interaction enables a fast rise time, which enables the desired output pulse to drive the LED array 319 in this embodiment.

The aforementioned micro controller 312, which gives instructions to the Digital Potentiometer ICs 305, is also utilized to set up pulse rates, cycle time, and the period time for the oscillations. The micro controller 312 additionally controls the LED wave length selection, and manages the eventual output of the device 300. To control the wavelength of the device 300, the micro controller 312 sends instructions to LED multi wave length select diver/multiplexer 327. To control the output, the micro controller 312 utilizes thermal switch 320 to monitor the thermal temperature of the LED array/dies in the multi-wavelength LED array 319. The micro controller 312 also monitors intensity feedback from a photo transistor and amplifier detector circuit 326; based on the feedback received, the micro controller 312 makes corrections as needed.

This micro controller 312 is triggered and stopped by a start stop switch 313. The pulse time selection of the micro controller 312 is triggered by a pulse select time switch 314. Thus, the micro controller 312 receives input from two switches, the start/stop switch 313, and the pulse time select switch 314; these inputs direct the activity of the micro controller 312.

The activities of the microcontroller 312 and of the device itself can be monitored using the liquid crystal display (LCD) 315. The display can display to a user the settings controlled by the micro controller 312 so the user can make manual adjustments throughout different procedures. An embodiment of the present invention may include a camera in the fiber optics assembly. The LCD 315 would then display the images captured and guide the user of the device 300 in the dental procedure.

In this embodiment of the present invention, the heat is managed in order to keep the system cool; the cooler the LED dies, the greater the output power. To cool the system, the device 300 utilizes a cooling fan 316 to remove heat from the thermoelectric heat pump 318, and heat sink 317. This thermoelectric heat pump 318 is attached to the heat sink 317 and the LED array/dies in the multi-wavelength LED array 319.

The light emanating from the multi-wavelength LED array 319 is refocused into a focal point by optical lens 321. Further embodiments of the present invention may employ alternative optical components such as reflectors, mirrors and/or prisms, to refocus and direct the light into a focal point. After the light is refocused, it is sent through a fiber optics assembly 322 that interfaces with the multi-wavelength LED array 319 and a fiber optic cable 323, the latter of which attaches to a hand piece 324 that attaches to a removable tip 325. The tip 325 disperses the light at one or more predetermined angles of refraction and the resultant output (light) creates effective oscillations in the liquid. The material comprising the tip includes but is not limited to plastic and/or glass.

The device 400 in FIG. 4, like the device 300 of FIG. 3, utilizes an LED light source. Referring to FIG. 4, the device 400 is powered by an AC or DC input 401 and a DC voltage power supply 402. Serving a role similar to the micro controller 312 of FIG. 3, in FIG. 4, an LED driver 403 controls the period, cycle, and pulse generation of the light source, in this embodiment, a single or multi-wave LED array (die) 405. This LED driver 403 is coupled to a start/stop switch 404, which triggers and stops the oscillations.

The light source for the photon induced photo acoustic streaming in this device 400 is a single or multi-wave LED array (die) 405. Embodiments capable of multiple wavelengths are useful across more diverse applications, but depending upon the application, the use of a single wavelength LED array may be sufficient and therefore, an embodiment with only a single wavelength is cost effective.

Figure 6:
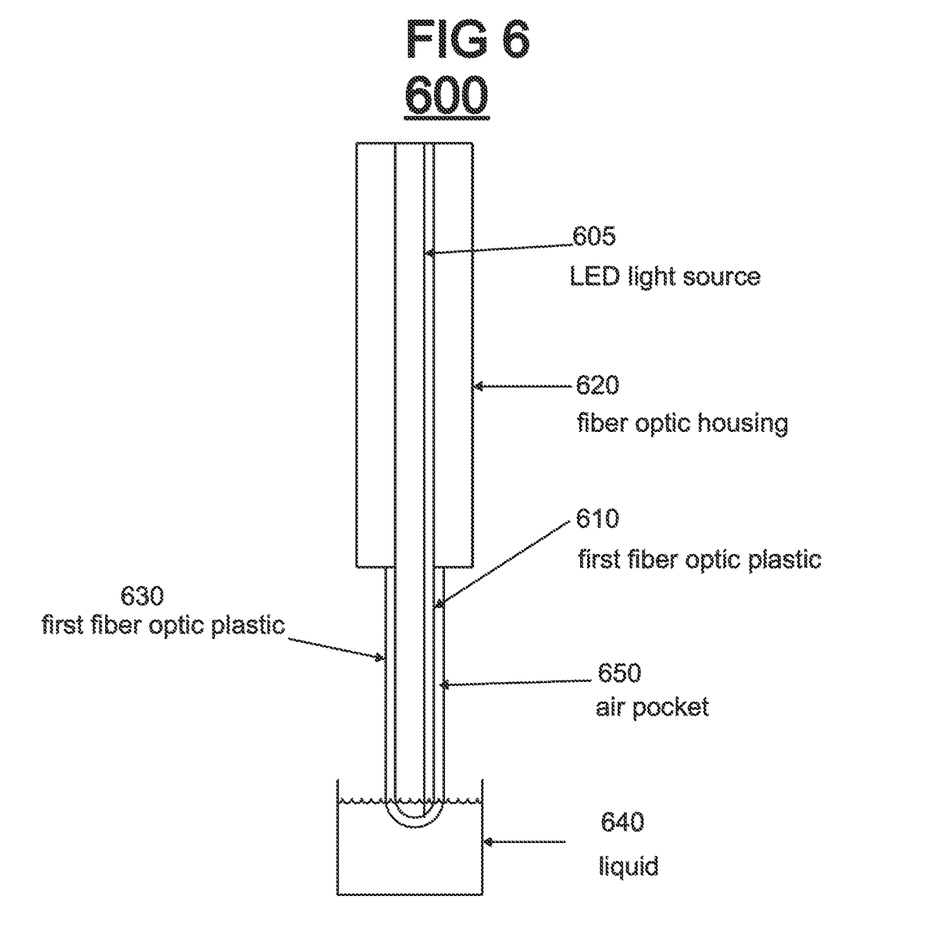
FIG. 6 depicts an embodiment of an aspect of the present invention.

The light from the light source, in FIG. 4, the single or multi-wavelength LED array (die) 405, is focused by an optical device, such as the displayed optic lens 406, but including, but not limited to, one or more lenses, reflectors, mirrors, and/or prisms. After the light is refocused and directed, it travels through a fiber optics assembly 410, to a fiber optic cable 407, which attaches to a hand piece 408, which holds a removable tip 409. The tip 409 outputs the light in a predetermined pattern so that the resultant output (light) oscillates the liquid into which the tip is partially submerged. The material comprising the tip includes but is not limited to plastic and/or glass. FIG. 6 is an embodiment of a removable tip 407.

Figure 5:
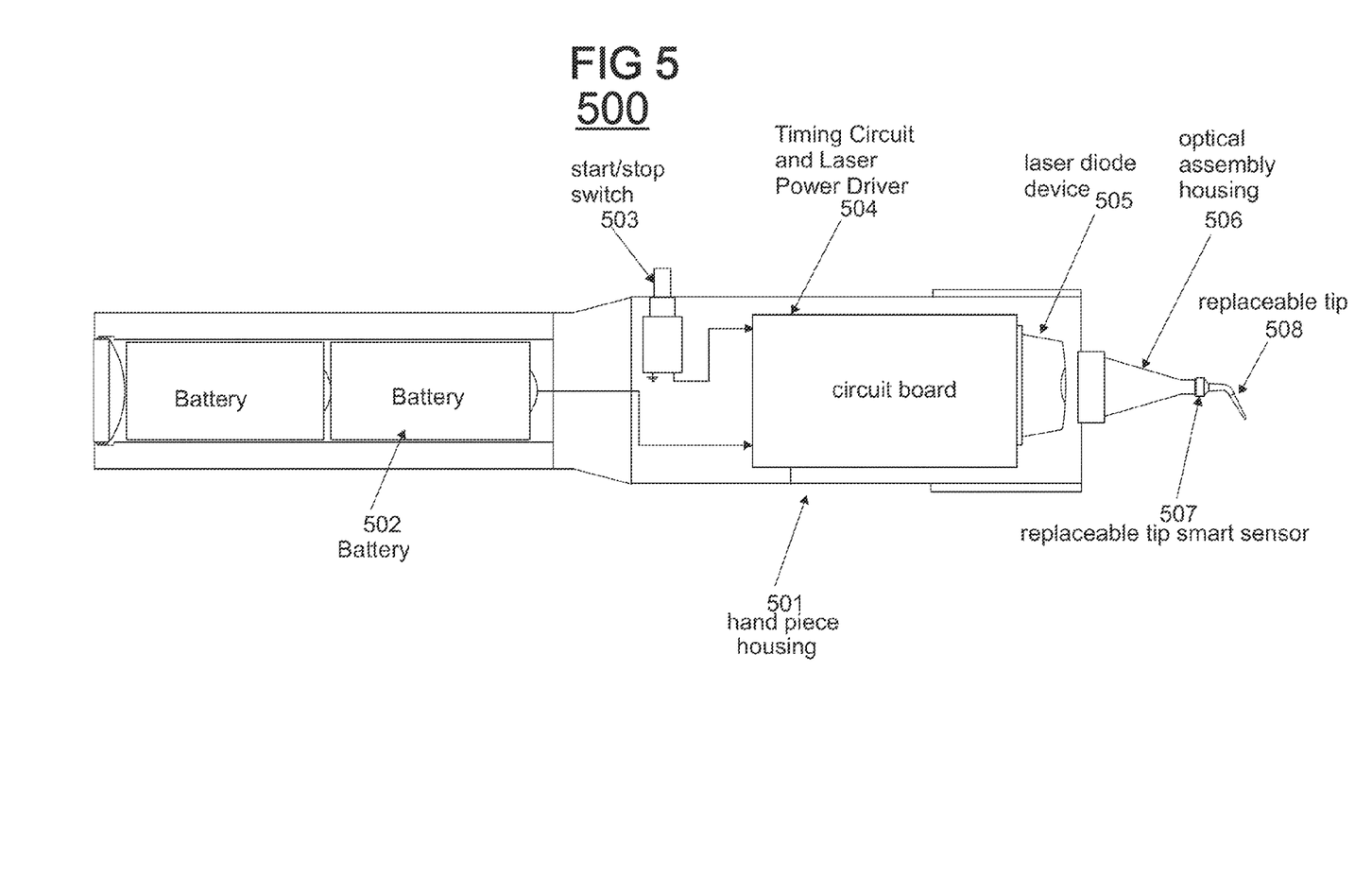
FIG. 5 depicts an embodiment of the present invention.

The embodiment of FIG. 5 utilizes a laser diode as a light source. The device 500 of FIG. 5 uses two batteries 502 are a power source. The portion of the device 500 that houses the batteries connects to the hand piece housing 501. In this embodiment, a start/stop switch 503 initiates the timing circuit and laser power driver 504 for the laser diode device 505, that generates the wavelengths for the photo acoustic treatments. Attached to the hand piece housing 501, is the optical housing assembly 506, which includes replaceable tip smart sensor 507 and the replaceable tip 508, examples of which are described in FIGS. 6 and 8a, 8b, and 8c.

The smart sensor 507 is a safety feature in this embodiment. These sensors are small contacts that are imbedded in the head of the replaceable tip, they set the program for the power level of the light source, for example, the LED or laser array. Endodontics requires a higher power setting than periodontics. If you were to attempt to utilize the high power settings of an endodontic application for a periodontic application, the smart sensors 507 could sense the issue and adjust accordingly.

In an embodiment of the present invention, the smart sensor 507 recognizes the replaceable tip 508 as either a high power tip, a low power tip, or bio stimulation tip, and then sets the power and settings automatically so the operator cannot use the replaceable tip for an incorrect application and/or with improper settings.

Across the varied light sources utilized in this apparatus and method, the tip is an output tip for the IR vibrational absorption spectrum of liquid water and directs light from the source to a focal point, and/or spreads it out to cover a broad optical pattern. Embodiments of this tip are both disposable and non-disposable. However, for sanitary reasons, non-disposable tips must be made of materials that can be sterilized.

Referring to FIG. 6, components of this embodiment of the tip 600 are comprised of fiber optic plastic. The tip isolates the light that passes through it from the liquid it will pulse. This tip 600 can be incorporated into various embodiments of the present invention, including but not limited to the embodiments of FIGS. 1-5. The light from the source, which in this embodiment is an LED 605, is encased in an in a first fiber optic plastic 610, which disperses the light at various angles. The angle(s) of refraction may be established by cutting the fiber optic cable at a certain angle and/or including a refracting device in the first fiber optic layer 610, such as a lens, mirror, and/or prism.

A fiber optic housing 620 surrounds the portion of the tip 600 that does not come into contact with liquid 640. The goal of this tip is to prevent the distortion of the refracted light, even when the tip 600 comes into contact with liquid. Allowing the first fiber optic plastic 610 to contact the liquid, would distort the angles. This change in the medium would cause the light and the heat to converge, creating a hot spot, which would damage the tissue and teeth of a patient. A hot spot could also cause pain. To this end, a second fiber optic plastic 630 surrounds the end of the tip. The second fiber optic plastic 630 prevents the liquid from making contact with the main optical surface, so the light is not distorted by the liquid 640. Instead of the refracted light coming into contact with the liquid and the angle being compromised, the space between the first fiber optic plastic 610 and the second fiber optic plastic 630, creates an air pocket 650. The contact with the air will not change the angle. The second fiber optic layer 630 also preserves the angle if the tip 600 comes into contact with any structure in the mouth of a patient.

The angle(s) of refraction achieved by the tip will vary across embodiments of the tip and across applications. For example, a tip that is being used during a root canal may refract light in a variety of directions to irrigate unreachable tissue pockets. Meanwhile, some embodiments used in periodontics may focus the light to a single point upon exiting the tip 600.

Figure 7:
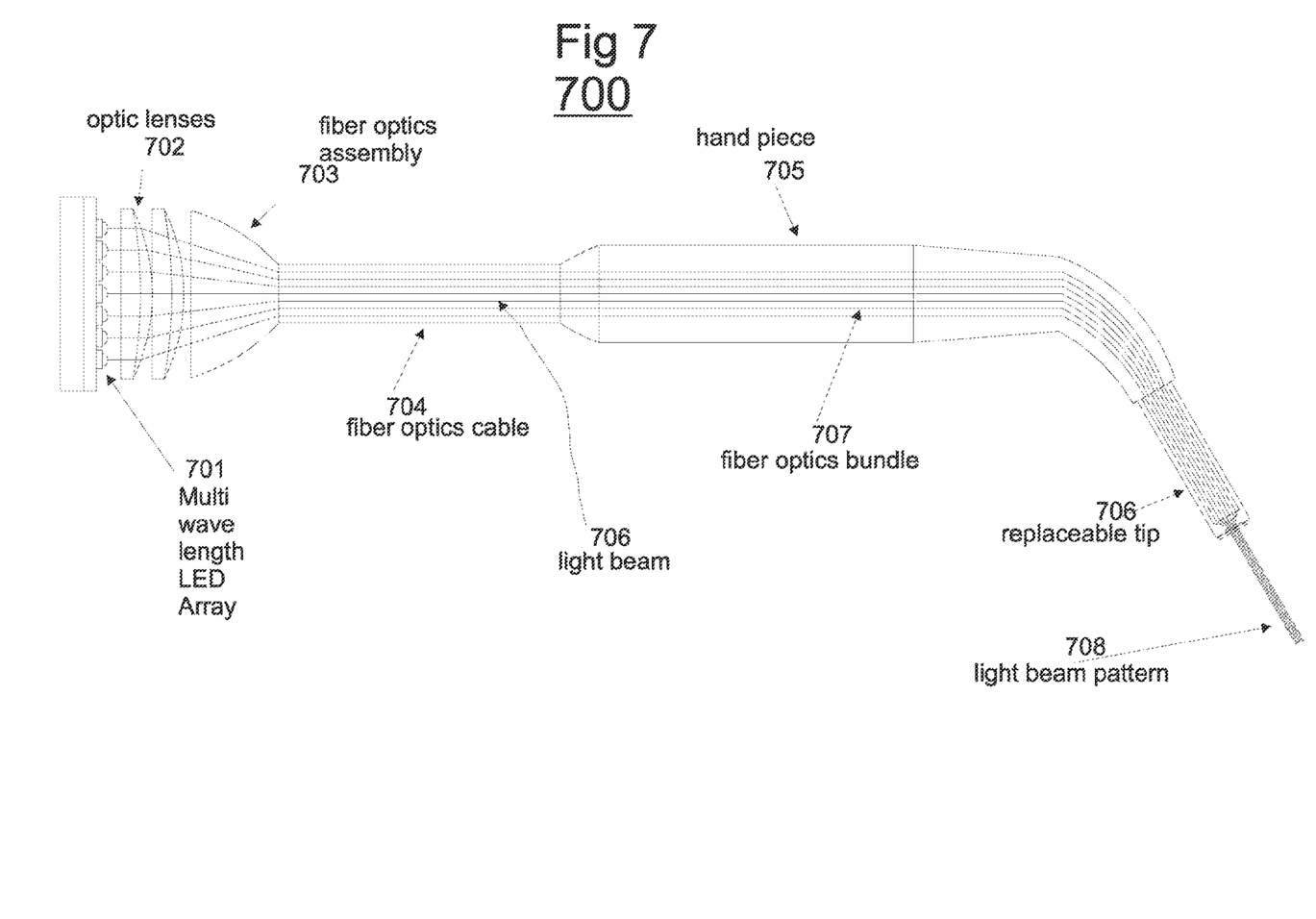
FIG. 7 depicts an embodiment of an aspect of the present invention.

FIG. 7 depicts a portion of an embodiment of the apparatus 700 of the present invention. Referring to FIG. 7, the light source, a multi-wavelength LED array, emits light, which is gathered and focused by two optics lenses 702. One of skill in the art will recognize that further embodiments of the present invention can utilize different structures with equivalent functionality to the optic lenses 702 to gather and focus light, including but not limited to one or more reflectors, mirrors and/or more prisms, and/or a combination of these items.

After the light is refocused, the light beam 706 is sent through a fiber optics assembly 703 and into a fiber optics cable 704. The fiber optics bundle 707 in the fiber optics cable 704 is enclosed by a hand piece 705, to which a replaceable tip 706 is attached. As seen in FIG. 6, the replaceable tip 706 prevents the light emanating from the fiber optics bundle 707, from coming into direct contact with liquid because of a pocket between the end of the fiber optics cable 704 and the end of the replaceable tip 706. The light beam pattern 708 output from the replaceable tip 706 is preserved because the light does not output directly into liquid, which could potentially create hotspots. The material comprising the tip includes but is not limited to plastic, glass, and/or a high temperature optic fiber material, such as acrlate.

Figure 8A:
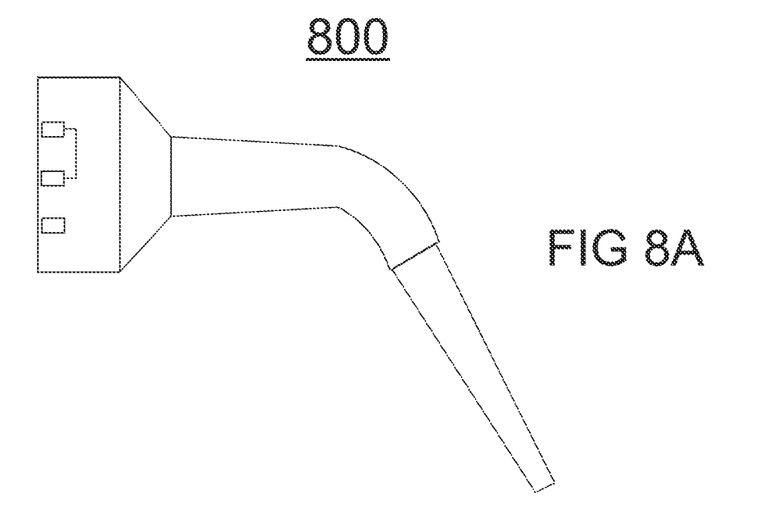
FIGS. 8a-8c depicts an embodiment of an aspect of the present invention.
Figures 8B, 8C:
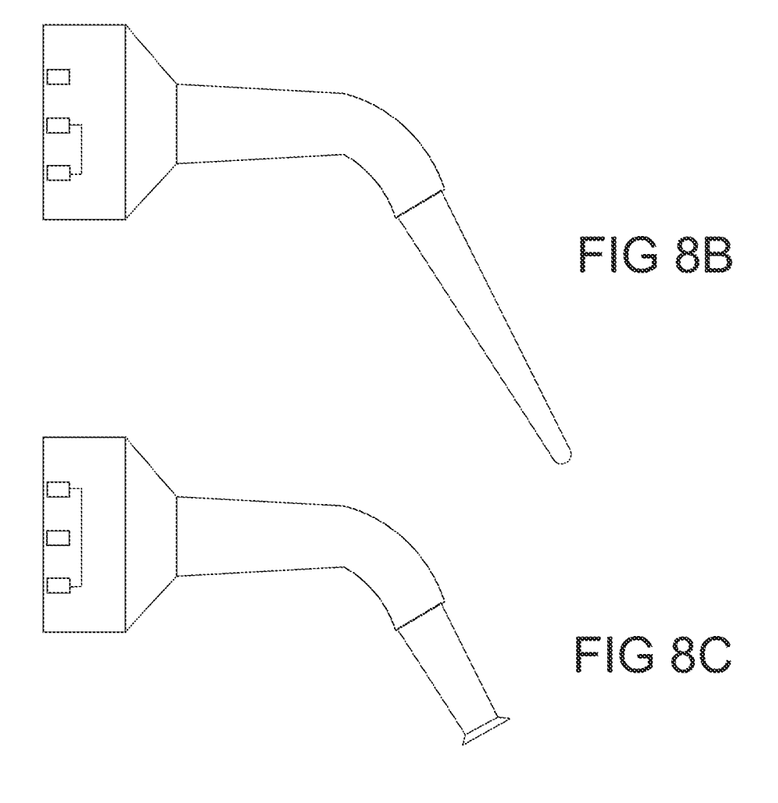

FIGS. 8a-8c depict three embodiments of replaceable tips that are utilized by an embodiment of the present invention for both endodontic and periodontic applications. The different shapes of the ends of these tips apply the light and photo acoustic emissions in different patterns that are suited for these different applications.

FIG. 8a depicts a Photo Induced Streaming Tip, which is designed to send a photo acoustical shock wave through irrigation materials, including but not limited to, a solution of 17% Ethylenediaminetetraacetic acid (EDTA), and 5.25% sodium hypochlorite. As aforementioned, any anti-bacterial and/or antimicrobial solution, saline solution, and/or water can be used in conjunction with embodiments of this tip.

FIG. 8b depicts a Perio High Energy Tip, which is designed to decontaminate and eliminate pathogenic bacteria dispersed through the pocket and on the tooth structure. In an embodiment of the present invention, this tip is used for cutting soft tissue in the sulcus, or gum tissue of the mouth. This procedure is performed when the tissue is either badly infected or is too high on the tooth and does not allow easy access for brushing and flossing.

Embodiments of the present invention are also used in conjunction with a lower energy tip than that depicted in 8b. The lower energy allows the light source to be focused, but not so greatly where it performs a cutting task, but rather is diffused and diluted where it allows for bactericidal effects within the periodontal pocket. This would include killing pathogens that are attached to the tooth, or laying on the outside layer of the periodontal tissue. Utilizing this lower energy tip can be used for a longer period of time, or with higher energy, to treat diseased tissue itself which has absorbed pathogens into the tissue which cannot be removed by normal SRP (scaling and root planning), and are only effectively removed with a light therapy or a heavy antibiotic treatment, the latter of which is not always effective. The diameter of the low energy tip is wider to allow for a less concentrated application of light and acoustic waves.

FIG. 8c depicts a Perio Biostimulation Tip, which is designed to biostimulate cell function and repair to promote increased lymphatic flow, production of endorphins, increased microcirculation, increased collagen formation and to stimulation of fibroblasts. This tip utilizes a low energy setting and the tip is wide so it spreads acoustic waves over a larger area. Thus, the light source, such as a laser diode, affects damaged tissue, but not healthy tissue. The light emitted normalizes cell function and promotes healing and repair.

The targeted values in the IR vibrational absorption spectrum for water utilized by embodiments of the present invention will vary in accordance with the embodiment, as well as the application.

Different wavelengths are effective for different applications. Certain wavelengths have been effective in removal of calculus of the tooth and root surface. Certain wavelengths have been effective in stimulation of bone growth where there has been slight to moderate bone loss due to advanced periodontal disease. By varying one or more of the pulse rate, power settings, and/or tip, this range is effective across multiple applications.

In an embodiment of the present invention, a wavelength of 950-980 nm is utilized for both endodontic and periodontic applications. By varying the repetitive rate (Hz), duty cycle, and pulse duration, (i.e., the power settings), in addition to the spectrum, an embodiment utilizing this wavelength is effective and available using various power/ light sources. Light sources include, but are not limited to, incandescent bulbs, HIDs, LEDs, and laser diodes. In this embodiment, the power settings can be configured to emit 10-15 Hz utilizing 20 microjoules with 50 millisecond bursts during photo induced streaming for endodontic and periodontic applications. In general, endodontic applications will utilize higher power settings while periodontic applications utilize lower power settings. Additional embodiment of the present invention employ lower wavelengths for periodontic applications coupled with lower power settings.

As aforementioned, the apparatus of the present invention is capable of utilizing one or more wavelengths in a single embodiment. By varying the power settings, some wavelengths are effective across multiple applications. However, some embodiments of the present invention are capable of wavelengths that are particularly effective for certain applications. For example, embodiments that emit wavelengths of 500 nm-1064 nm, are particularly effective in periodontic treatments. Embodiments that emit wavelengths of 950 nm-980 nm are particularly effective in endodontic treatments because in this lower range, absorption increases. For example, the absorption rate at 950-980 nm is approximately ten times greater than the rate when utilizing a wavelength in the 600s range. However, an embodiment of the present invention utilizing a 514 nm wavelength, though not the most effective as far as absorption, is capable of photo acoustic streaming for endodontic applications. The 950-980 nm range is merely suggested and not limiting. Embodiments of the present invention utilize wavelengths up to 3300 nm for endodontic applications.

Regardless of the light source utilized in an embodiment of the present invention, the wavelengths utilized are flexible across ranges. For example, some embodiments with LEDs range from 350 nm-3300 nm. Some embodiments with laser diodes range from 375 nm-3500 nm. Some embodiments with HIDs range from 500 nm-1950 nm. Some embodiments with incandescent sources range from 500-1950 nm. These embodiments are merely offered by way of example. One of skill in the art will recognize that the present apparatus and method can be configured and practiced by varying the wavelengths beyond the described embodiments.

The power utilized by various embodiments varies in accordance with the wavelength and power source of the selected embodiment. Embodiments of the present invention utilize cycle times of 1 Hz to 250 Hz and pulses timed of 1 micro second to 1000 micro seconds. One of skill in the art will recognize that the present apparatus and method can be configured and practiced by varying the cycle times and pulse timings and rates beyond the described embodiments.

Although the present invention has been described in relation to particular embodiments thereof, many other variations and modifications will become apparent to those skilled in the art. As such, it will be readily evident to one of skill in the art based on the detailed description of the presently preferred embodiment of the apparatus, system and method explained herein, that different embodiments can be realized.

The invention claimed is:

1. A photon-induced acoustic streaming device for endodontic and periodontic applications, comprising:
   a power source;
   a trigger coupled to the power source;
   circuit elements initiated by the trigger, wherein the circuit elements comprise a timing circuit and a driver;
   a light source coupled to the circuit elements wherein the driver controls one or more of a period, a duty cycle, and a pulse generation of the light source to create photon induced acoustic waves; and
   an optical assembly coupled to the light source wherein the optical assembly comprises a fiber optic cable and an output tip, through which the photon induced acoustic waves exit the output tip in a pre-determined pattern, wherein the output tip comprises:
      a fiber optic housing surrounding an upper portion of the tip wherein the fiber optic housing is adjacent to the light source;
      a first fiber optic plastic coupled to the fiber optic housing and surrounding a lower portion of the output tip; and
      a second fiber optic plastic surrounding the first fiber optic plastic wherein the first fiber optic plastic and the second fiber optic plastic are separated by an air pocket.

2. The device of claim 1, wherein the optical assembly refracts light from the light source.

3. The device of claim 1, wherein the light source comprises at least one of: an incandescent bulb, a high intensity discharge lamp, a light emitting diode, a laser diode.

4. The device of claim 1, wherein the optical assembly further comprises an optic element configured to focus the light from the light source before the light moves through the fiber optic cable.

5. The device of claim 4, wherein the optic element comprises at least one of: a lens, a reflector, a mirror, a prism.

6. The device of claim 1, wherein the output tip is detachable from the device optical assembly.

7. The device of claim 1, wherein light exits the output tip through the first fiber optic plastic, through the air pocket and through the second fiber optic plastic.

8. The device of claim 1, wherein the second fiber optic plastic is positioned to contact liquid when the trigger is engaged.

9. The device of claim 1, wherein the light source emits light at more than one predetermined wavelength comprising a first predetermined wavelength to perform an endodontic procedure and a second predetermined wavelength to perform a periodontic procedure.

10. The device if claim 1, wherein the predetermined pattern is comprised of light focused into a single point.

11. The device of claim 1, wherein the power source comprises a battery.

12. The device of claim 1, wherein the trigger comprises a start/stop switch.

13. A method utilizing a photon-induced acoustic streaming device for endodontic and periodontic applications, the method comprising:
   obtaining a photon-induced acoustic streaming device, comprising:
      a power source;
      a trigger coupled to the power source;
      circuit elements initiated by the trigger, wherein the circuit elements comprise a timing circuit and a driver;
      a light source coupled to the circuit elements wherein the driver controls one or more of a period, cycle, and pulse generation of the light source to create photon induced acoustic waves; and
      an optical assembly coupled to the light source wherein the optical assembly comprises a fiber optic cable and an output tip, through which the photon induced acoustic waves exit the output tip in a pre-determined pattern;
   engaging a trigger on a handheld assembly of the device to trigger a light source to emit light at a first predetermined wavelength; and
   positioning a lower portion of the output tip in an irrigation fluid to emit photon induced acoustic waves from the output tip into the irrigation fluid to irrigate dental canals and structures coming into contact with the irrigation fluid, wherein the lower portion of the output tip comprises a first fiber optic plastic and a second fiber optic plastic, the second fiber optic plastic surrounding the first fiber optic plastic with an air pocket separating the first fiber optic plastic and the second fiber optic plastic.

14. The method of claim 13, further comprising:
   adjusting the wavelength on the device to trigger the light source to emit light at a second predetermined wavelength; and
   positioning the lower portion of the output tip proximate to diseased tissue to emit photon induced wavelengths from the output tip to perform at least one of the following: eliminate bacteria in the diseased tissue, remove calculus, remove biofilm, cut soft tissue, remove of soft tissue, disinfect a periodontal pocket, biostimulate dental structures.

15. The method of claim 14 wherein the first pre-determined wavelength is greater than or equal to 950 nm and less than or equal to 980 nm and the second pre-determined wavelength is greater than or equal to 500 nm and less than or equal to 1064 nm.

16. The method of claim 13, wherein the irrigation fluid comprises 17% Ethylenediaminetetraacetic acid and 5.25% sodium hypochlorite.

17. The method of claim 13, further comprising:
   adjusting at least one of the repetitive rate, the duty cycle, and the pulse duration of the device; and positioning the output tip proximate to diseased tissue to emit photon induced wavelength from the output tip to perform at least one of the following:
   eliminate bacteria in the diseased tissue, remove calculus, remove biofilm, cut soft tissue, remove of soft tissue, disinfect a periodontal pocket, biostimulate dental structures.

18. The method of claim 17, wherein the lower portion of the output tip comprises a first fiber optic plastic and a second fiber optic plastic, the second fiber optic plastic surrounding the first fiber optic plastic with an air pocket intermediate to the first fiber optic plastic and the second fiber optic plastic.

19. A device for photon induced endodontic and periodontic applications, comprising:
   a power source;
   a trigger coupled to the power source;
   circuit elements initiated by the trigger, wherein the circuit elements comprise a timing circuit and a driver;
   a light source coupled to the circuit elements wherein the driver controls one or more of a period, a duty cycle, and a pulse generation of the light source to create photon induced acoustic waves; and an optical assembly coupled to the light source wherein the optical assembly comprises a fiber optic cable and an output tip, wherein said output tip is adapted for at least one of: removal of calculus, removal of biofilm, cutting soft tissue, removal of soft tissue, periodontal pocket disinfection, biostimulation, wherein the output tip comprises:
- a fiber optic housing surrounding an upper portion of the tip wherein the fiber optic housing is adjacent to the light source;
- a first fiber optic plastic coupled to the fiber optic housing and surrounding a lower portion of the output tip; and
- a second fiber optic plastic surrounding the first fiber optic plastic wherein the first fiber optic plastic and the second fiber optic plastic are separated by an air pocket.

20. The device of claim 19, wherein the light source comprises at least one of: an incandescent bulb, a high intensity discharge lamp, a light emitting diode, a laser diode.

\* \* \* \* \*